United States Patent
Kamata et al.

(10) Patent No.: US 7,955,792 B2
(45) Date of Patent: Jun. 7, 2011

(54) DILUENT FOR NOROVIRUS OR SAPOVIRUS SPECIMEN AND METHOD FOR DETECTING VIRUS

(75) Inventors: Kunio Kamata, Gosen (JP); Daisuke Kato, Gosen (JP)

(73) Assignee: Denka Seiken Co., Ltd., Tokyo (JP)

( * ) Notice: Subject to any disclaimer, the term of this patent is extended or adjusted under 35 U.S.C. 154(b) by 675 days.

(21) Appl. No.: 10/551,548

(22) PCT Filed: Mar. 31, 2004

(86) PCT No.: PCT/JP2004/004687
§ 371 (c)(1),
(2), (4) Date: Sep. 30, 2005

(87) PCT Pub. No.: WO2004/088311
PCT Pub. Date: Oct. 14, 2004

(65) Prior Publication Data
US 2006/0216695 A1    Sep. 28, 2006

(30) Foreign Application Priority Data

Mar. 31, 2003  (JP) ................................. 2003-095349

(51) Int. Cl.
*C12Q 1/70*    (2006.01)
*C12P 21/00*   (2006.01)
(52) U.S. Cl. .......................................... 435/5; 435/70.1
(58) Field of Classification Search ............... 424/130.1; 530/387.1; 435/7.1
See application file for complete search history.

(56) References Cited

U.S. PATENT DOCUMENTS
2004/0073006 A1    4/2004    Kageyama et al.

FOREIGN PATENT DOCUMENTS
JP    8-500250    1/1996
JP    2003-095349    3/2003
WO    91/07502    5/1991
WO    WO 91/05817 A1 *    5/1991
WO    02/40509    5/2002

OTHER PUBLICATIONS

Neth. J. Path. 1982, vol. 99, pp. 171-183.*
Brinker et al. J. Clin. Micro. 1998, vol. 36, No. 4. pp. 1064-1069.*
Hansman et al. J. Clin. Micro. 2004, vol. 42, No. 3, pp. 1305-1307.*
Yoda et al. J. Clin. Micro. 2003, vol. 41, No. 6, pp. 2367-2371.*
Hill et al. Proceeding—Water Quality Technology Conference 2002, pp. 672-283.*
Bicova et al. J. chromatography A, 1999, vol. 852, pp. 141-149.*
Holdworth et al. Planta, 1987, vol. 172, No. 4, pp. 539-547.*
Hibi J. Gen. Viol: 1985, vol. 66, pp. 1191-1194.*
Gibco BRL Life Techonologies (2000-2001 catalog, p. 26.*
Martinez et al. J. Med. Virol. 2001, vol. 67, pp. 289-298.*
Kitamoto et al. J. Clin. Microbiol., Jul. 2002;40(7):2459-65.*
Hardy et al. Virology, 1996, vol. 217, pp. 252-261.*
Kobayashi et al. J. Med. Virol, 2000, vol. 62, pp. 233-238.*
wikipedia.org/wiki/Good's_buffers (pp. 1-2, Sep. 9, 2008.*
ICTVdB Index of Viruses, Jun. 2002.*
Hale et al. Clinical and Diagnostic Virology 1996, vol. 5, pp. 27-35.*
Good's buffers published by SIGMA-ALDRICH on line, search on Feb. 25, 2009.*
Atmar et al. Clin. Micro. Review 2001, vol. 14, No. 1, pp. 15-37.*
Ausar et al. J. Biological. Chemistry, 2006, vol. 281, No. 28, pp. 19478-19488.*
Greenberg, Harry B. et al.: "Proteins of Norwalk Virus" Journal of Virology, vol. 37, No. 3, pp. 994-999, Mar. 1981.

* cited by examiner

*Primary Examiner* — Bao Li
(74) *Attorney, Agent, or Firm* — Oblon, Spivak, McClelland, Maier & Neustadt, L.L.P.

(57) ABSTRACT

The present invention relates to a diluent for a Norovirus or Sapovirus specimen, the diluent containing an alkaline buffer of pH 9.0 to 10.0, and to a method for detecting a Norovirus or a Sapovirus through use of the diluent. According to the present invention, a Norovirus or a Sapovirus can be detected in a Norovirus- or Sapovirus-containing specimen such as stool, vomit, body fluid, blood, body tissue, or food, in a convenient manner without use of a special machine such as a centrifuge, with an improved detection sensitivity, and with complete elimination of non-specific factors.

18 Claims, No Drawings

DILUENT FOR NOROVIRUS OR SAPOVIRUS SPECIMEN AND METHOD FOR DETECTING VIRUS

TECHNICAL FIELD

The present invention relates to a method for enhancing detection sensitivity of an immunoassay of Noroviruses or Sapoviruses contained in a specimen of, for example, stool, vomit, body fluid, blood, body tissue, or food; and to a method for preventing non-specific reactions.

BACKGROUND ART

Viruses belonging to the human Caliciviridae, such as Norovirus (previously called the Norwalk virus) and Sapovirus (previously called the Sapporo virus), cause acute enterogastritis in humans. In most cases, stool specimens are used to detect these viruses. In general, ELISA or a similar assay performed on stool specimens is problematic in that not only is its detection sensitivity low, but it also accompanies a lot of non-specific reactions. Therefore, it has been difficult to elucidate results of the assay. In order to improve detection sensitivity, there is a conventional means useful for detecting an antibody that exhibits high reactivity with the antigen. However, such an antibody is too hard to prepare. Incidentally, in order to prevent non-specific reactions which might occur when a stool specimen is employed, a variety of preliminary treatment methods have been performed. Examples of such methods include centrifugation of a specimen to precipitate nonspecific-reaction-related factors for removal and removal of lipids by use of an organic solvent, etc. However, these methods are cumbersome and requires a special apparatus; i.e., a centrifuge. There is another method in which a specimen is suspended in a buffer to which a surfactant added. This method is problematic in that, if non-specific reactions are completely eliminated, its specific reaction weakens whereas if reduction in the incident of specific reactions is prevented, non-specific reactions cannot be avoided completely.

DISCLOSURE OF THE INVENTION

Thus there has been a growing demand for convenient means capable of improving detection sensitivity when a Norovirus- or Sapovirus-containing specimen of, for example, stool, vomit, body fluid, blood, body tissue, or food, is used, without requiring a centrifuge or a similar special apparatus, and also means for completely eliminating non-specific factors.

In view of the foregoing, the present inventors carried out extensive studies on a method for detecting a Norovirus or a Sapovirus through immunoassay by use of a specimen such as stool, and came to the finding that, when a specimen is treated with a diluent for specimen (hereinafter referred to as "specimen diluent"), the diluent containing an alkaline buffer of pH 9.0 to 10.0, the detection sensitivity can be improved in a convenient manner. The present inventors also found that, when an animal globulin, a surfactant, a water-soluble polymer, or a similar substance is added to the specimen diluent or when the salt concentration of the specimen diluent is optimized, it is possible to remove non-specific reactions, and as a consequence, accurate immunoassay detection of a Norovirus or a Sapovirus becomes possible without use of a process such as centrifugation.

Accordingly, the present invention provides a diluent for a Norovirus or Sapovirus specimen, containing an alkaline buffer of pH 9.0 to 10.0.

The present invention also provides a diluent for a Norovirus or Sapovirus specimen, containing an alkaline buffer of pH 9.0 to 10.0 and an animal globulin, a surfactant, or a water-soluble polymer.

The present invention also provides a reagent for detecting a Norovirus or a Sapovirus, the reagent containing an anti-Norovirus antibody or an anti-Sapovirus antibody and the above-described diluent for a Norovirus or Sapovirus specimen.

The present invention also provides a method for detecting a Norovirus or a Sapovirus in a specimen, characterized in that the above-described diluent for a Norovirus or Sapovirus specimen is added to the specimen, and the thus-obtained specimen-containing solution is reacted with an immobilized anti-Norovirus antibody or anti-Sapovirus antibody.

BEST MODE FOR CARRYING OUT THE INVENTION

Examples of the specimen employed in the present invention include a stool, a vomit, a food, a body fluid, a blood, a body tissue which may be contain a Norovirus or a Sapovirus. Among them, a stool, a vomit, and a food are preferred, with a stool being more preferred.

The object to be detected according to the present invention is a Norovirus or a Sapovirus, with a Norovirus being preferred.

An alkaline buffering agent employed for providing a diluent for a Norovirus or Sapovirus specimen in the present invention is capable of forming a buffer having a pH of 9.0 to 10.0. When the buffer has a pH of lower than 9.0 or higher than 10.0, the detection sensitivity cannot be improved sufficiently.

Examples of the buffer having a pH of 9.0 to 10.0 include Tris buffer, Good's buffer, borate buffer, and carbonate buffer, with Tris buffer and Good's buffer being particularly preferred.

In the present invention, detection sensitivity can be improved by diluting a specimen with a buffer having a pH of 9.0 to 10.0 while its mechanism remains to be elucidated. However, it is considered that, at the pH conditions, virus particles are disintegrated to thereby allow epitopes within the virus particles to be exposed, resulting in enhancement in antigen-antibody reaction. In other words, for example, a Norovirus has, within the virus particle, an epitope shared by every type of Norovirus strains, and, typically, the epitope is not exposed from the virus particle. When the virus is treated with an alkaline buffer having a pH of 9.0 to 10.0, and the shared epitope within the virus particle is exposed, the reactivity is enhanced, and detection sensitivity is improved.

Preferably, an animal globulin is incorporated into the specimen diluent in an amount of 0.01 to 1.0 mg/mL, preferably 0.01 to 0.5 mg/mL, more preferably 0.05 to 0.5 mg/mL, to efficiently prevent non-specific reactions. Preferred examples of the animal globulin include those derived from mouse, rabbit, sheep, and human.

Preferably, a surfactant is incorporated into the specimen diluent to efficiently prevent non-specific reactions. The surfactant is preferably a nonionic surfactant or an amphoteric surfactant. Examples of the nonionic surfactant include polyethylene glycol alkyl phenyl ethers such as polyethylene glycol mono-p-isooctyl phenyl ether (Triton X100) and polyoxyethylene sorbitan mono-fatty acid esters such as polyoxyethylene sorbitan monolaurate (Tween 20).

Examples of the amphoteric surfactant include sulfobetain amphoteric surfactants such as 3-[(3-cholamidopropyl)dimethylamino]1-propane sulfonate (CHAPS). The amount of the surfactant incorporated into the specimen diluent is preferably 0.01 to 5.0% by mass, more preferably 0.02 to 2.0% by mass, from the viewpoint of effective prevention of non-specific reactions. When the surfactant is polyethylene glycol alkyl phenyl ether, the amount incorporated is preferably 0.5 to 5.0% by mass, more preferably 1.0 to 2.0% by mass. When the surfactant is a polyoxyethylene sorbitan mono-fatty acid ester, the amount incorporated is preferably 0.01 to 0.1% by mass, more preferably 0.02 to 0.08% by mass. When the surfactant is a sulfobetain amphoteric surfactant, the amount incorporated is preferably 0.05 to 2.0% by mass, more preferably 0.1 to 0.5% by mass.

Preferably, a water-soluble polymer is incorporated into the specimen diluent to prevent non-specific reactions efficiently. Examples of the water-soluble polymer include polyvinyl pyrrolidone (PVP), dextran sulfate, polyethylene glycol, and polyvinyl alcohol. Among them, polyvinyl pyrrolidone is particularly preferred. The water-soluble polymer is incorporated preferably in an amount of 0.1 to 8.0% by mass, more preferably 0.2 to 5.0% by mass, from the viewpoint of effective prevention of non-specific reactions.

Preferably, a serum albumin, in particular fetal bovine serum albumin (BSA), is incorporated into the specimen diluent. The amount of the serum albumin incorporated is preferably 0.1 to 1.0% by mass, more preferably 0.5% by mass.

When the salt concentration of the specimen diluent falls into a range of 1 to 8% by mass, particularly 2 to 4% by mass, non-specific reactions are prevented more effectively. This concentration contains that of the alkaline buffer. Examples of the salt employed include alkali metal salts such as NaCl and KCl, alkaline earth metal salts such as $CaCl_2$, and amino acid salts such as arginine hydrochloride.

Treatment of a specimen with a specimen diluent may be performed by adding the specimen diluent to the specimen and leaving the diluted specimen to stand for 5 minutes or longer, preferably 10 minutes or longer, more preferably 10 minutes to 2 hours. The treatment temperature is preferably 4 to 37° C., more preferably 20 to 25° C. When the specimen thus-treated is subjected to a common immunoassay through use of an anti-Norovirus antibody or an anti-Sapovirus antibody, Norovirus or Sapovirus can accurately be detected with improved detection sensitivity, since non-specific reactions are prevented.

No particular limitation is imposed on the method for detecting a Norovirus or a Sapovirus, so long as the method employs an immunoassay through use of an anti-Norovirus antibody or an anti-Sapovirus antibody. However, preferred is a sandwich method employing an anti-Norovirus antibody or an anti-Sapovirus antibody and a labeled anti-Norovirus antibody or a labeled anti-Sapovirus antibody. More preferred is a method employing an immobilized anti-Norovirus antibody or an immobilized anti-Sapovirus antibody and a labeled anti-Norovirus antibody or a labeled anti-Sapovirus antibody.

Each of the anti-Norovirus antibody and the anti-Sapovirus antibody may be any of a monoclonal antibody or a polyclonal antibody. Examples of the monoclonal antibody include monoclonal antibodies against Noroviruses described in the 47th Meeting of the Japanese Society of Virology (Nov. 7th, 1999); Virology, Vol. 217, 252-261 (1996); J. Clin. Microbiol., Vol. 38, 1656-1660 (2000); J. Clin. Microbiol., Vol. 40, 2459-2465 (2002); and JP-A-2002-20399 and 2002-17397. Examples of the polyclonal antibody include a polyclonal antibody against a Norovirus described in Japanese Sai-Kohyo (PCT) Patent Publication WO00/079280.

Each of these antibodies is preferably immobilized to an insoluble support such as a polystyrene plate, latex particles, magnetic particles, a glass fiber film, a nylon film, a nitrocellulose film, or a cellulose acetate film.

A labeling substance employed to form a labeled anti-Norovirus antibody or a labeled anti-Sapovirus antibody may be a known labeling substance such as a radioisotope (e.g., $^{32}P$, $^{35}S$, $^{3}H$), an enzyme (e.g., peroxydase, alkaline phosphatase, luciferase), a protein (e.g., avidin), a low molecule compound (e.g., biotin), a fluorescent substance (e.g., FITC), a chemiluminescent substance (e.g., acridinium), latex particles (e.g., colored latex particles, fluorescent latex particles), a metal (e.g., a noble metal such as gold, silver, or platinum), colloid particles, or carbon atoms.

Detection of a Norovirus or a Sapovirus in a specimen is performed by adding the above-described specimen diluent to the specimen, and reacting the thus-obtained specimen-containing solution with immobilized antibody. When a sandwich method is employed, typically, the specimen-containing solution is reacted with immobilized antibody and then with the above-described labeled antibody. However, in the present invention, by use of the specimen-containing solution prepared through use of the specimen diluent according to the present invention, accurate measurement is made possible even when the specimen is reacted simultaneously with immobilized antibody and labeled antibody. In this simultaneous method, a diluted specimen is added to a plate having anti-Norovirus antibody or anti-Sapovirus antibody immobilized thereto, and, immediately after that, labeled antibody is added. The simultaneous method is different from a typical method in which a diluted specimen is added to an antibody-immobilized plate to cause reaction therebetween, the plate is washed, and then labeled antibody is added. In the present invention, use of the simultaneous method enables not only convenient measurement as compared with a typical method, but also reduction in non-specific reactions.

After completion of reaction, the amount of the labeling substance contained in the complex formed between a Norovirus or a Sapovirus in the specimen, immobilized antibody, and labeled antibody is measured, to determine the amount of the Norovirus or the Sapovirus contained in the specimen. Measurement of the labeling substance may be performed through use of a technique which depends on the type of the labeling substance. For example, when an enzyme or avidin is employed as a labeling substance, after completion of reaction, a substrate is added, and the enzymatic activity is determined. When a fluorescent substance (including fluorescent latex particles) or a chemiluminescent substance is employed as a labeling substance, a signal is measured under conditions which permit no occurrence of quenching. When colored latex particles, metal colloid particles, or carbon particles are employed, signal measurement is performed visually or through use of, for example, reflection.

The detection method according to the present invention preferably employs ELISA or immunochromatography, particularly preferably ELISA.

The detection reagent according to the present invention essentially contains the above-described specimen diluent and any of the above-described antibodies. Preferably, the detection reagent further contains any of the above-described labeled antibodies. Specifically, the detection reagent preferably contains the above specimen diluent, an immobilized anti-Norovirus antibody or an immobilized anti-Sapovirus antibody, and a labeled anti-Norovirus antibody or a labeled anti-Sapovirus antibody.

EXAMPLES

The present invention will next be described in more detail by way of examples, which should not be construed as limiting the invention thereto.

Example 1

Improvement in Sensitivity by use of Alkaline Buffer

Anti-Norovirus monoclonal antibody NV3912 (J. Clin. Microbiol., Vol. 38, 1656-1660 (2000)) capable of broadly recognizing Noroviruses of genotype I (GenogroupI: GI) and anti-Norovirus monoclonal antibody NS14 (J. Clin. Microbiol., Vol. 40, 2459-2465 (2002)) capable of broadly recognizing Noroviruses of genotype II (GenogroupII: GII) were respectively diluted with a carbonate buffer (pH 9.4) to a concentration of 5 µg/mL. Each of the resultant mixtures was dispensed to a polystyrene flat-type microplate (product of Nunc) (100 µL/well). The thus-prepared microplate was left to stand at 4° C. overnight. After having been left to stand for 18 hours or more, the microplate was washed twice with 10 mM PBS (200 µL/well) containing Tween 20 at a final concentration of 0.05%. Subsequently, 10mM PBS (pH 7.2) supplemented with bovine serum albumin (BSA) and Tween 20 (0.5% and 0.05%, respectively; final concentration) was added thereto. (200 µL/well). The microplate was left to stand at 4° C. overnight, to thereby produce a microplate on which anti-Norovirus monoclonal antibodies had been immobilized.

To each of an antigen prepared from Norovirus strain 124 belonging to GI through the recombinant method and an antigen prepared from Norovirus strain 1876 belonging to GII through the recombinant method, an alkaline buffer (20 mM Tris-HCl pH 9.0, 0.5% BSA, 0.05% Tween 20) or a neutral buffer (PBS pH 7.2, 0.5% BSA, 0.05% Tween 20) was added, to produce diluted antigen solutions having different antigen concentrations (0.1, 1.0, and 10.0 ng/mL). Subsequently, the resultant solutions were left to stand for 10 minutes or 60 minutes.

Each of the above-obtained diluted antigen solutions (100 µL) containing GI recombinant Norovirus antigen (strain 124) was added to the wells of the microplate on which anti-Norovirus monoclonal antibody NV3912 had been immobilized and each of the above-obtained diluted antigen solutions (100 µL) containing GII recombinant Norovirus antigen (strain 1876) was added to the wells of the microplate on which anti-Norovirus monoclonal antibodies NS14 had been immobilized, followed by reaction at 25° C. for 1 hour. After completion of reaction, the reaction mixture was removed by aspiration. Subsequently, 10mM PBS (pH 7.2) containing Tween 20 at a final concentration of 0.05% was added to the wells (200 µL/well), followed by a similar aspiration procedure. This addition and aspiration procedure was repeated at least three times. POD-labeled anti-GI Norovirus polyclonal antibody which had been diluted to an optimum concentration by use of 10 mM PBS (pH 7.2) supplemented with BSA and Tween 20 (0.5% and 0.05%, respectively; final concentration) was added to the wells to which a diluted solution of GI recombinant antigen had been added, and POD-labeled anti-GII polyclonal antibody which had been diluted to an optimum concentration by use of 10 mM PBS (pH 7.2) supplemented with BSA and Tween 20 (0.5% and 0.05%, respectively; final concentration) was added to the wells to which a diluted solution of GII recombinant antigen had been added, followed by reaction at 25° C. for 1 hour. After completion of reaction, the reaction mixture was removed by aspiration. Subsequently, 10 mM PBS (pH 7.2) containing Tween 20 at a final concentration of 0.05% was added to each well (200 µL/well), followed by a similar aspiration procedure. This addition and aspiration procedure was repeated at least five times. Subsequently, TMB solution (100 µL) containing hydrogen peroxide was added to the wells, followed by reaction at room temperature for 30 minutes. After completion of reaction, 0.6N sulfuric acid (100 µL) was added to each well, and absorbance (450 nm/630 nm) of the wells was measured by means of an ELISA autoreader.

TABLE 1

| Reaction time | | 10 minutes | | 60 minutes | |
|---|---|---|---|---|---|
| Buffer pH | | pH 7.2 | pH 9.0 | pH 7.2 | pH 9.0 |
| NV3912 | | | | | |
| 124 | 10.0 | 0.712 | 1.995 | 0.602 | 1.991 |
| strain | 1.0 | 0.108 | 0.253 | 0.095 | 0.228 |
| ng/mL | 0.1 | 0.045 | 0.047 | 0.049 | 0.048 |
| | BLK | 0.047 | 0.079 | 0.049 | 0.048 |
| NS14 | | | | | |
| 1876 | 10.0 | 1.067 | 4.619 | 1.032 | 5.937 |
| strain | 1.0 | 0.140 | 1.173 | 0.138 | 0.817 |
| ng/mL | 0.1 | 0.032 | 0.121 | 0.034 | 0.102 |
| | BLK | 0.022 | 0.023 | 0.023 | 0.027 |

As shown in Table 1, when a buffer of pH of 9.0 or higher was used, increase in absorbance was found to be at least nearly two times larger than the case where a buffer of pH 7.2 was used. The increase in absorbance was also shown 60 minutes after the start of the reaction. In one of the strains, the longer the reaction time, the larger the increase in absorbance.

Example 2

Effect of Surfactant

Triton X100, which is a surfactant, was added to an alkaline buffer, to thereby produce specimen diluents (Triton X100 concentration: 0, 1, 2, and 3%).

Each of the thus-prepared specimen diluents (10 mL) was added to each of the stool samples (0.5 to 1.0 g) collected from patients infected with Norovirus. The resultant mixture was suspended and left to stand for 10 minutes. The supernatant was collected, and a 10% stool sample suspension was prepared therefrom. The resultant suspension (100 µL) was added to the wells of the microplate on which anti-Norovirus monoclonal antibodies had been immobilized, followed by reaction at 25° C. for 1 hour. After completion of reaction, the reaction mixture was removed by aspiration. Subsequently, 10 mM PBS (pH 7.2) containing Tween 20 at a final concentration of 0.05% was added to the wells (200 µL/well), followed by a similar aspiration procedure. This addition and aspiration procedure was repeated at least three times. Subsequently, POD-labeled anti-Norovirus polyclonal antibody which had been diluted to an optimum concentration by use of 10 mM PBS (pH 7.2) supplemented with BSA and Tween 20 (0.5% and 0.05%, respectively; final concentration) was added to the wells, followed by reaction at 25° C. for 1 hour. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least five times. Subsequently, TMB solution (100 μL) containing hydrogen peroxide was added to the wells, followed by reaction at room temperature for 30 minutes. After completion of reaction, 0.6N sulfuric acid (100 μL) was added to the wells, and absorbance (450 nm/630 nm) of the wells was measured by means of an ELISA autoreader.

TABLE 2

| Specimens | Surfactant Concentration | Triton X100 | | | |
|---|---|---|---|---|---|
| | | 0% | 1% | 2% | 3% |
| NV3912 | | | | | |
| Stool specimens from patients infected with Norovirus | 124 | 0.498 | 0.422 | 0.378 | 0.490 |
| | 258 | 2.335 | 2.718 | 2.750 | 3.239 |
| | 18-3 | 0.107 | 0.015 | 0.015 | 0.018 |
| | 1876 | 0.105 | 0.015 | 0.022 | 0.019 |
| Stool specimens from healthy subjects | D10 | 0.114 | 0.034 | 0.042 | 0.045 |
| | D12 | 0.134 | 0.014 | 0.015 | 0.014 |
| | D16 | 0.100 | 0.023 | 0.028 | 0.029 |
| | BLK | 0.049 | 0.033 | 0.039 | 0.041 |
| NS14 | | | | | |
| Stool specimens from patients infected with Norovirus | 124 | 0.224 | 0.045 | 0.048 | 0.053 |
| | 258 | 0.202 | 0.044 | 0.043 | 0.045 |
| | 18-3 | 0.254 | 0.182 | 0.181 | 0.190 |
| | 1876 | 1.840 | 1.639 | 2.071 | 1.788 |
| Stool specimens from healthy subjects | D10 | 0.463 | 0.114 | 0.133 | 0.138 |
| | D12 | 0.312 | 0.033 | 0.034 | 0.036 |
| | D16 | 0.211 | 0.066 | 0.065 | 0.068 |
| | BLK | 0.097 | 0.113 | 0.127 | 0.132 |

Table 2 reveals that, when the NV3912-immobilized plate was employed, the stool specimen suspensions which had been prepared through use of specimens collected from healthy subjects or from patients infected with a Norovirus belonging to GII and then diluted with the specimen diluent containing no surfactant exhibited high absorbance as compared with that of the blank, suggesting non-specific reactions. However, the stool specimen suspensions which had been prepared through use of specimens collected from healthy subjects or from patients infected with a Norovirus belonging to GII and then diluted with the specimen diluent containing Triton X100 at a concentration of 1% or higher exhibited absorbance levels which are similar to that of the blank, suggesting diminished non-specific reactions. Similarly, when the NS14-immobilized plate was employed, the stool specimen suspensions which had been prepared through use of specimens collected from healthy subjects and from patients infected with a Norovirus belonging to GI exhibited absorbance levels which are equal to or lower than that of the blank, suggesting diminished non-specific reactions.

Example 3

Effect of Mouse Globulin

Mouse globulin was added to an alkaline buffer containing Triton X100 as a surfactant (Triton X100 concentration; 1%), to thereby produce specimen diluents (Mouse globulin concentration; 0, 0.1, 0.01, and 0.001 mg/mL).

Each of the thus-prepared specimen diluents (10 mL) was added to each of the stool samples (0.5 to 1.0 g) collected from patients infected with Norovirus. The resultant mixture was suspended and left to stand for 10 minutes. The supernatant was collected, and a 10% stool sample suspension was prepared therefrom. The resultant suspension (100 μL) was added to the wells of the microplate on which anti-Norovirus monoclonal antibody had been immobilized, followed by reaction at 25° C. for 1 hour. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least three times. Subsequently, POD-labeled anti-Norovirus polyclonal antibody which had been diluted to an optimum concentration by use of 10 mM PBS (pH 7.2) supplemented with BSA and Tween 20 (0.5% and 0.05%, respectively; final concentration) was added, followed by reaction at 25° C. for 1 hour. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least five times. Subsequently, TMB solution (100 μL) containing hydrogen peroxide was added to the wells, followed by reaction at room temperature for 30 minutes. After completion of reaction, 0.6N sulfuric acid (100 μL) was added to each well, and absorbance (450 nm/630 nm) of the wells was measured by means of an ELISA autoreader.

TABLE 3

| Specimens | Globulin Concentration mg/mL | Mouse globulin fractions | | | |
|---|---|---|---|---|---|
| | | 0 | 0.1 | 0.01 | 0.001 |
| NV3912 | | | | | |
| Stool specimens from patients infected with Norovirus | 258 | 5.942 | 4.812 | 4.254 | 4.364 |
| | 1876 | 0.075 | 0.039 | 0.044 | 0.066 |
| Stool specimens from healthy subjects | D10 | 0.064 | 0.035 | 0.038 | 0.038 |
| | D16 | 0.074 | 0.038 | 0.037 | 0.033 |
| | BLK | 0.075 | 0.036 | 0.045 | 0.054 |
| NS14 | | | | | |
| Stool specimens from patients infected with Norovirus | 258 | 0.080 | 0.038 | 0.040 | 0.074 |
| | 1876 | 2.110 | 2.102 | 2.114 | 2.143 |
| Stool specimens from healthy subjects | D10 | 0.044 | 0.036 | 0.039 | 0.043 |
| | D16 | 0.041 | 0.020 | 0.024 | 0.032 |
| | BLK | 0.056 | 0.030 | 0.027 | 0.057 |

Table 3 shows that, when specimen diluents containing mouse globlin were employed, the blank and the stool specimen suspensions which had been prepared through use of specimens collected from patients infected with a Norovirus belonging to GII or from healthy subjects and then diluted with the specimen diluents containing mouse globulin exhibited absorbance levels, which are lowered by about 2 times as compared to the absorbance as measured in the case in which specimen diluents containing no mouse globulin were employed. Similarly, when the NS14-immobilized plate was employed, absorbance as measured in the case where mouse globulin was added was found to be lower than that of the case where no mouse globulin was added. This indicates that, through addition of mouse globulin, non-specific reactions can be reduced.

Example 4

Optimization of Salt Concentration

Specimen diluents (salt concentration: 1, 2, or 8%) were produced from an alkaline buffer (mouse globulin concentration: 0.1 mg/mL, Triton X100 concentration: 1%).

Each of the thus-prepared specimen diluents (10 mL) was added to each of the stool samples (0.5 to 1.0 g) collected from patients infected with Norovirus. The resultant mixture was suspended and left to stand for 10 minutes. The supernatant was collected, and a 10% stool sample suspension was prepared therefrom. The resultant suspension (100 μL) was added to the wells of the microplate on which anti-Norovirus monoclonal antibody had been immobilized, followed by reaction at 25° C. for 1 hour. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least three times. Subsequently, POD-labeled anti-Norovirus polyclonal antibody which had been diluted to an optimum concentration by use of 10 mM PBS (pH 7.2) supplemented with BSA and Tween 20 (0.5% and 0.05%, respectively; final concentration) was added to the wells, followed by reaction at 25° C. for 1 hour. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least five times. Subsequently, TMB solution (100 μL) containing hydrogen peroxide was added to the wells, followed by reaction at room temperature for 30 minutes. After completion of reaction, 0.6N sulfuric acid (100 μL) was added to the wells, and absorbance (450 nm/630 nm) of the wells was measured by means of an ELISA autoreader.

TABLE 4

| Specimens | Plate | NV3912 | NS14 |
|---|---|---|---|
| NaCl 1% | | | |
| Stool specimens from patients infected with Norovirus | 124 | 0.712 | 0.026 |
| | 1876 | 0.011 | 0.369 |
| Stool specimens from healthy subjects | D10 | 0.086 | 0.109 |
| | BLK | 0.024 | 0.090 |
| NaCl 2% | | | |
| Stool specimens from patients infected with Norovirus | 124 | 0.726 | 0.021 |
| | 1876 | 0.010 | 0.414 |

TABLE 4-continued

| Specimens | Plate | NV3912 | NS14 |
|---|---|---|---|
| Stool specimens from healthy subjects | D10 | 0.017 | 0.055 |
| | BLK | 0.028 | 0.087 |
| NaCl 8% | | | |
| Stool specimens from patients infected with Norovirus | 124 | 0.534 | 0.039 |
| | 1876 | 0.011 | 0.325 |
| Stool specimens from healthy subjects | D10 | 0.014 | 0.038 |
| | BLK | 0.032 | 0.057 |

From the data in Table 4, it has been concluded that the final salt concentration of a specimen diluent at which the reactivity of the stool specimens from patients infected with Norovirus is least affected while the reactivity of the stool samples from healthy subjects is reduced is 2%.

Example 5

Effect of Water-soluble Polymer

Polyvinylpyrrolidone (PVP), which is a water-soluble polymer was added to an alkaline buffer, to produce specimen diluents (final polyvinylpyrrolidone (PVP) concentration: 0.2, 1.0, or 5.0%).

Each of the thus-prepared specimen diluents was added to Norovirus recombinant antigen (antigen concentration: 1 ng/mL), and the mixture was left to stand for 10 minutes, to thereby produce a diluted antigen solution. Each of the above-prepared specimen diluents (10 mL) was added to each of the stool samples (0.5 to 1.0 g) from healthy subjects. The resultant mixture was suspended, and left to stand for 10 minutes. The supernatant was collected, and a 10% stool sample suspension was prepared therefrom. The diluted antigen solution and the 10% stool sample suspension (100 μL each) were each added to the wells of the microplate on which anti-Norovirus monoclonal antibodies had been immobilized, and POD-labeled anti-Norovirus polyclonal antibody which had been diluted to an optimum concentration by use of 10 mM PBS (pH 7.2) supplemented with BSA and Tween 20 (0.5% and 0.05%, respectively; final concentration) was immediately added to the wells to which the 10% stool sample suspension had been added, followed by reaction at 25° C. for 2 hours. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least five times. Subsequently, TMB solution (100 μL) containing hydrogen peroxide was added to the wells, followed by reaction at room temperature for 30 minutes. After completion of reaction, 0.6N sulfuric acid (100 μL) was added to the wells, and absorbance (450 nm/630 nm) of the wells was measured by means of an ELISA autoreader.

TABLE 5

| | Specimens | Absorbance |
|---|---|---|
| PVP 0% | VLP124 | 4.755 |
| | VLP18-3 | 0.867 |
| | D10 | 0.203 |
| | D16 | 0.159 |
| | D17 | 0.074 |

TABLE 5-continued

|  | Specimens | Absorbance |
|---|---|---|
| PVP 0.2% | VLP124 | 4.876 |
|  | VLP18-3 | 0.877 |
|  | D10 | 0.173 |
|  | D16 | 0.146 |
|  | D17 | 0.062 |
| PVP 1% | VLP124 | 4.525 |
|  | VLP18-3 | 0.807 |
|  | D10 | 0.145 |
|  | D16 | 0.120 |
|  | D17 | 0.055 |
| PVP 5% | VLP124 | 3.615 |
|  | VLP18-3 | 0.721 |
|  | D10 | 0.115 |
|  | D16 | 0.079 |
|  | D17 | 0.041 |
|  | BLK | 0.084 |

As shown in Table 5, non-specific reactions were reduced through addition of PVP. When specimen diluents containing PVP at a final concentration of 5.0% were employed, the absorbance of the stool specimens from healthy subjects was lowered by two times at maximum as compared with the case in which specimen diluents containing no PVP were employed. Thus, addition of PVP is thought to be effective in reduction of non-specific reactions.

Example 6

Method in Which a Specimen and a POD-labeled Antibody are Simultaneously Added to Wells of a Microplate Specimen diluents (salt concentration: 1, 2, 8%) were produced from an alkaline buffer (mouse globulin concentration: 0.1 mg/mL, Triton X100 concentration: 1%).

Each of the thus-prepared specimen diluents (10 mL) was added to each of the stool samples (0.5 to 1.0 g) collected from patients infected with Norovirus. The resultant mixture was suspended and left to stand for 10 minutes. The supernatant was collected, and a 10% stool sample suspension was prepared therefrom. The resultant suspension (100 μL) was added to the wells of the microplate on which anti-Norovirus monoclonal antibodies had been immobilized, and POD-labeled anti-Norovirus polyclonal antibody which had been diluted to an optimum concentration by use of 10 mM PBS (pH 7.2) supplemented with BSA and Tween 20 (0.5% and 0.05%, respectively; final concentration) was immediately added to the wells to which the 10% stool sample suspension had been added, followed by reaction at 25° C. for 2 hours. After completion of reaction, the reaction mixture was removed by aspiration. Subsequently, 10 mM PBS (pH 7.2) containing Tween 20 at a final concentration of 0.05% was added to the wells (200 μL/well), followed by a similar aspiration procedure. This addition and aspiration procedure was repeated at least five times. Subsequently, TMB solution (100 μL) containing hydrogen peroxide was added to the wells, followed by reaction at room temperature for 30 minutes. After completion of reaction, 0.6N sulfuric acid (100 μL) was added to the wells, and absorbance (450 nm/630 nm) of the wells was measured by means of an ELISA autoreader.

TABLE 6

| Stool specimens from healthy subjects | Typical method | Simultaneous method |
|---|---|---|
| NV3912 |  |  |
| DW3 | 0.211 | 0.011 |
| DW4 | 0.091 | 0.011 |
| DW5 | 0.124 | 0.011 |
| DW6 | 0.084 | 0.010 |
| D10 | 0.399 | 0.009 |
| D16 | 0.109 | 0.007 |
| D17 | 0.189 | 0.008 |
| D18 | 0.193 | 0.009 |
| BLK | 0.085 | 0.013 |
| NS14 |  |  |
| DW3 | 0.083 | 0.017 |
| DW4 | 0.061 | 0.017 |
| DW5 | 0.074 | 0.017 |
| DW6 | 0.057 | 0.029 |
| D10 | 0.125 | 0.026 |
| D16 | 0.062 | 0.013 |
| D17 | 0.095 | 0.012 |
| D18 | 0.088 | 0.013 |
| BLK | 0.064 | 0.019 |

As shown in Table 6, in the method employing simultaneous addition (i.e., a method in which a specimen and a POD-labeled antibody are simultaneously added to wells of a microplate), stool specimens collected from healthy subjects and blank exhibited low absorbance levels as compared with the typical method (i.e., a method in which a specimen is reacted with immobilized MAbs, the plate is washed, and POD-labeled antibodies are added). Therefore, as for the manipulation technique of ELISA, a method employing simultaneous addition of a specimen and a POD-labeled antibody to wells of a microplate was found to be more effective in reduction of non-specific reactions.

The invention claimed is:

1. A method for detecting a Norovirus in a specimen comprising:
    providing a specimen in an alkaline specimen buffer at a pH ranging from 9 to 10;
    contacting said specimen with an immobilized anti-Norovirus antibody for a time and under conditions sufficient for binding to occur, wherein contacting between the specimen and antibody takes place at a pH ranging from 9 to 10; and
    detecting binding between the specimen and the anti-Norovirus antibody thereby detecting Norovirus in the specimen;
    wherein said alkaline specimen buffer optionally comprises at least one ingredient selected from the group consisting of an animal globulin, a surfactant, a water-soluble polymer and a salt.

2. The method of claim 1, further comprising contacting said specimen with a second labeled anti-Norovirus antibody.

3. The method of claim 1, which is a sandwich method wherein said specimen is contacted with an immobilized anti-Norovirus antibody and then simultaneously or subsequently contacted with labeled anti-Norovirus antibody.

4. The method of claim 1, wherein said specimen is a food.

5. The method of claim 1, wherein said specimen is a bodily tissue, blood or another bodily fluid, vomit or stool.

6. The method of claim 1, wherein said specimen buffer contains an animal globulin.

7. The method of claim 1, wherein said specimen buffer contains a surfactant.

8. The method of claim 1, wherein said specimen buffer contains a water-soluble polymer.

9. The method of claim 1, wherein said specimen buffer contains a salt.

10. A method for detecting a Sapovirus in a specimen comprising:
   providing a specimen in an alkaline specimen buffer at a pH ranging from 9 to 10;
   contacting said specimen with an immobilized anti-Sapovirus antibody for a time and under conditions sufficient for binding to occur, wherein contacting between the specimen and antibody takes place at a pH ranging from 9 to 10; and
   detecting binding between the specimen and the anti-Sapovirus antibody thereby detecting Sapovirus in the specimen;
   wherein said alkaline specimen buffer optionally comprises at least one ingredient selected from the group consisting of an animal globulin, a surfactant, a water-soluble polymer and a salt.

11. The method of claim 10, further comprising contacting said specimen with a second labeled anti-Sapovirus antibody.

12. The method of claim 10, which is a sandwich method wherein said specimen is contacted with an immobilized anti-Sapovirus antibody and then simultaneously or subsequently contacted with labeled anti-Sapovirus antibody.

13. The method of claim 10, wherein said specimen is a food.

14. The method of claim 10, wherein said specimen is a bodily tissue, blood or another bodily fluid, vomit or stool.

15. The method of claim 10, wherein said specimen buffer contains an animal globulin.

16. The method of claim 10, wherein said specimen buffer contains a surfactant.

17. The method of claim 10, wherein said specimen buffer contains a water-soluble polymer.

18. The method of claim 10, wherein said specimen buffer contains a salt.

\* \* \* \* \*